United States Patent
Kross

(10) Patent No.: US 6,284,152 B1
(45) Date of Patent: Sep. 4, 2001

(54) COMPOSITIONS AND METHODS FOR STORING AQUEOUS CHLORINE DIOXIDE SOLUTIONS

(76) Inventor: Robert D. Kross, P.O. Box 374, Bellmore, NY (US) 11710

( * ) Notice: Subject to any disclaimer, the term of this patent is extended or adjusted under 35 U.S.C. 154(b) by 0 days.

(21) Appl. No.: 09/300,505

(22) Filed: Apr. 28, 1999

(51) Int. Cl.$^7$ ............... C01B 11/02; A61K 7/20
(52) U.S. Cl. ............... 252/187.21; 252/187.1; 252/187.23; 494/53; 494/661
(58) Field of Search ............... 252/187.1, 187.21, 252/187.23; 424/53, 661

(56) References Cited

U.S. PATENT DOCUMENTS

| | | |
|---|---|---|
| 3,123,521 | 3/1964 | Wentworth et al. . |
| 3,271,242 | 9/1966 | McNicholas et al. . |
| 4,144,374 | 3/1979 | Lagow et al. . |
| 4,536,266 | 8/1985 | Bliefert et al. . |
| 4,689,169 | 8/1987 | Mason et al. . |
| 4,721,654 * | 1/1988 | Richardson et al. ............... 428/474.4 |
| 4,829,129 | 5/1989 | Kelley . |
| 4,861,514 | 8/1989 | Hutchings . |
| 5,165,910 | 11/1992 | Oikawa et al. . |
| 5,252,343 * | 10/1993 | Kross ................... 424/661 |
| 5,707,546 * | 1/1998 | Pitochelli .................. 252/187.21 |
| 5,738,840 * | 4/1998 | Richter ................... 424/53 |

FOREIGN PATENT DOCUMENTS 959238   12/1974   (CA) .

OTHER PUBLICATIONS

Masschelein, W.J., *Chlorine Dioxide*, Rip G. Rice, ed. Ann Arbor Science, Ann Arbor, MI, 1979.
Gordon, Gilbert et al., *The Chemistry of Chlorine Dioxide*, Prog. Inorg. Chem 15: 201, pp. 234–286, 1972.

* cited by examiner

*Primary Examiner*—Jill Warden
*Assistant Examiner*—Monique T. Cole
(74) *Attorney, Agent, or Firm*—Coleman Sudol Sabone, P.C.

(57) ABSTRACT

The present invention is directed to both physical and chemical means for maintaining continuous high levels of chlorine dioxide in aqueous solutions for extended periods, with minimum loss through degradation in the solution and dissipation through the walls of the containing vessel within which the solution is stored. The $ClO_2$ may be maintained even in the absence of very high levels of chlorite, from which supplemental, offsetting levels of $ClO_2$ may be generated. The present invention relates to the discovery that certain types of plastic and glass containers have the ability to maintain relatively constant levels of $ClO_2$ in their contained solutions over extended periods, particularly in aqueous compositions comprising chlorite/$ClO_2$ ratios sufficient for a stabilizing complex of the two, presumably $Cl_2O_4^-$, to suppress the $ClO_2$ loss. Of particular value is certain high-density polyethylene terephthalate (PETE) plastic bottling and plastic containers which have been initially exposed to a fluorinating environment. Specifically, in the latter regard, it has been discovered that certain plastic containers which ordinarily are incapable of maintaining aqueous $ClO_2$ levels can be treated with fluorine gas to transform their surfaces so as to effectively suppress $ClO_2$ diffusion therethrough.

10 Claims, No Drawings

COMPOSITIONS AND METHODS FOR STORING AQUEOUS CHLORINE DIOXIDE SOLUTIONS

FIELD OF THE INVENTION

This invention relates generally to the stable storage of aqueous chlorine dioxide solutions in containers, and more particularly materials which minimize the diffusional loss of the gaseous molecule through the container walls, thereby allowing the commercialization of such solutions for disinfecting and deodorizing purposes.

BACKGROUND OF THE INVENTION

Chlorine dioxide ($ClO_2$) is a water-soluble gas, one of but a few compounds in nature which exist in a stable monomeric free radical form. In large part because of this structure, $ClO_2$ is a highly efficient antimicrobial and antiviral agent, as well as an oxidant of noxious odor molecules. It has found increasing utility as a disinfectant, deodorant and bleaching agent, in areas ranging from municipal water disinfection, reduction of oral halitosis and decolorizing paper pulp. $ClO_2$ is finding increased value as a replacement for chlorine in water and food disinfection because, unlike chlorine, it does not ordinarily produce chlorinated organic compounds which can be mutagenic and even carcinogenic. Unlike chlorine, it cannot be stored as a compressed gas, because the free radical molecule becomes explosive. As a result, for large scale use of $ClO_2$ such as in water disinfection or in chiller tanks of poultry processors, the gas must be generated on site. This is accomplished either through reduction of a chlorate salt, or the oxidation of a chlorite. Acidification of chlorite also yields high quantities of $ClO_2$ through disproportionation of the chlorous acid intermediate (Canadian Patent No. 959,238).

Aqueous $ClO_2$ solutions are generally considered to be inherently unstable, and to-date no one has attempted to offer stable, free-molecular $ClO_2$ solutions commercially, for its manifold applications. If a means were available to provide a simple aqueous solution of $ClO_2$ for industrial and home use, it would provide the consumer with an efficient and safe means for disinfecting and deodorizing home and commercial areas in unparalleled ways.

Aqueous $ClO_2$ solutions degrade in the following manner: $2\ ClO_2 + H_2O \rightleftharpoons ClO_2^- + ClO_3^- + 2H^+$. Although acidic solutions suppress the degradation, it is largely complete even in fairly acid environments. A product, ProFresh™, which is an oral deodorizing solution containing free molecular $ClO_2$, has been commercially distributed for a number of years, but its effective shelf life is limited to weeks or months because of continuing $ClO_2$ loss. There is also a great deal of confusion relating to so-called "stabilized chlorine dioxide" solutions, which have little or none of the free $ClO_2$ molecule, but which predominate instead in chlorite ion. The claim is made that during use, the unstable chlorite can lead to a slow generation of $ClO_2$ but not with sufficient rapidity to provide any significant $ClO_2$ activity. The "stabilization" of chlorine dioxide, by reaction of the $ClO_2$ with peroxides to form chlorite, has been taught in a number of patents, including those of Wentworth (U.S. Pat. No. 3,123,521) and McNicholas (U.S. Pat. No. 3,271,242). Other attempts to stably contain $ClO_2$ are found in U.S. Pat. No. 4,829,129, in which the molecule is claimed to be complexed with an organic polymer, and in U.S. Pat. No. 4,861,514, where $ClO_2$ is apparently maintained in a steady-state concentration, after its slow formation over many days, in a thickened aqueous solution comprising a gelling agent, a chlorite salt, and an aldehyde or acetal. In neither of these two patents does the resulting composition provide a simple stable solution, of freely-available $ClO_2$, appropriate for easy disinfecting or deodorizing applications, without the presence of other solutes necessary for $ClO_2$ stabilization. In addition, the application of the referenced compositions to a substrate intended for disinfection, would leave significant levels of dried residue upon evaporation of the aqueous solvent.

U.S. Pat. No. 5,165,910 teaches a method for preparing what is termed by the inventor to be a stabilized aqueous chlorine dioxide solution, by reacting an excess of alkali metal chlorite with an alkali metal hypochlorite and an acid in solutions at a pH of either 7–9 or 2–5.6. The $ClO_2$, is prepared from a solution comprising 0.1–5% of an alkali metal chlorite and 5–40 ppm of an alkali metal hypochlorite, which oxidizes a very small fraction of the metal chlorite to $ClO_2$. The initial molar ratio of alkali metal chlorite to alkali hypochlorite is from about 20 to 6000, and the ratio of metal chlorite to $ClO_2$ in the resulting solution is approximately the same. In the reference patent, the room-temperature storage of the resulting $ClO_2$ solution for a month, in an unspecified container, indicated no appreciable loss of $ClO_2$ at the alkaline pH, and only small losses at acidic pH's. When attempting to replicate these conditions, with storage of the resulting solutions in high-density polyethylene containers, the present inventor found that at least 50% of the $ClO_2$ was lost within 14 days. Thus the patent is not instructive in terms of practicing the present invention and verifying the claimed stability of the resulting $ClO_2$ solutions.

Accordingly, there is a long-felt need in the art for a means of providing a storage-stable chlorine dioxide solution, at concentrations appropriate for intermittent and extended use of the solution for a wide range of applications for which $ClO_2$ is unique. These uses are in the home, industrial and agricultural settings, and include, among others, the disinfection of food items, kitchen countertops and bathroom fixtures; reduction of oral malodor by oxidation of the sulfurbearing compounds responsible for halitosis as well as destruction of the putrefactive microorganisms responsible for the production of noxious odorants; the deodorization of pet animals, including the odor of skunks; disinfection of fresh picked raw fruits, vegetables and related agricultural products; and the bleaching of stained clothing in a safe manner.

There is a more particular need to identify specific container materials, including certain preferred techniques for producing such container materials, so that $ClO_2$ solutions may be properly maintained, with little or no loss of the $ClO_2$ by reaction with the container and/or permeation therethrough. The present invention is the direct result of investigations into means for minimizing or preventing loss of $ClO_2$ associated with the distribution of $ClO_2$-containing oral malodor treatment solutions in plastic containers, and led to surprising findings with respect to the properties of aqueous $ClO_2$ solutions.

OBJECTS OF THE INVENTION

It is an object of the present invention to provide plastic and glass containers which are effective for the stable storage of $ClO_2$ solutions.

It is an additional object of the invention to provide storage stable $ClO_2$ compositions.

It is yet another object of the invention to provide both physical and chemical means for maintaining continuous high levels of $ClO_2$ in aqueous solutions for extended periods with minimum loss through degradation, even in the absence of high levels of chlorite, which would normally shift the equilibrium to the formation of further levels of $ClO_2$.

It is still another object of the invention to provide convenient-to-use storage stable $ClO_2$ solutions which may be used to promote sterilization, disinfection and mouth-cleansing activity including reduction in halitosis which have heretobefore not been used to a large extent because of the inconvenience of producing effective amounts of $ClO_2$ using a two part acid/chlorite system.

The above-described objects of the present invention which may relate to one or more embodiments of the present invention and/or other objects of the invention may be readily gleaned from a review of the description which follows.

BRIEF DESCRIPTION OF THE INVENTION

In brief, the present invention is directed to a combination of physical and chemical means for maintaining continuous high levels of chlorine dioxide in aqueous solutions for extended periods, with minimum loss through degradation in the solution and dissipation through the walls of the containing vessel within which the solution is stored. The $ClO_2$ may be maintained even in the absence of very high levels of chlorite, from which supplemental, offsetting levels of $ClO_2$ may be generated. This is an unexpected result.

It has been discovered that certain types of plastic and glass containers have the ability to maintain relatively constant levels of $ClO_2$ in their contained solutions over extended periods, particularly in aqueous compositions comprising chlorite/$ClO_2$ ratios sufficient for a stabilizing complex of the two, presumably $C_2O_4^-$, to suppress the $ClO_2$ loss. Of particular value is a variety of high-density polyethylene terephthalate (PETE) plastic bottling and plastic containers which have been initially exposed to a fluorinating environment. Specifically, in the latter regard, it has been discovered that certain plastic containers which ordinarily are incapable of maintaining aqueous $ClO_2$ levels can be treated with fluorine gas to transform their surfaces so as to effectively suppress $ClO_2$ diffusion therethrough. This is a surprising finding inasmuch as such fluorinated surfaces do not reduce permeation and loss of gaseous molecules of even smaller size, such as oxygen, $O_2$. Indeed, fluorine polymers are actually known as being more oxygen permeable than hydrocarbon polymers.

An understanding of this phenomenon may derive from another surprising discovery that, while colorless or blue transparent PETE and both clear and colored glass containers (blue tinted, opaque white) can minimize $ClO_2$ losses, the same suppression is not observed for either brown-tinted PETE or colorless, transparent PETE containers whose outer surfaces have been covered with translucent tape. Without being limited by way of theory, the changed surface polarity or charge of the latter containers, as effected by the tape's adhesion, or the former by the nature of the colorant is presumed to be the source of this surprising difference.

Accordingly, the present invention is directed to $ClO_2$ containing-solutions, wherein the concentration of $ClO_2$ is at least about 1 ppm, preferably at least about 3 ppm of $ClO_2$, more preferably at least about 5 ppm up to as much as 500 ppm of $ClO_2$ in combination with chlorite ion ($ClO_2^-$). These solutions are preferably stored in a $ClO_2$ diffusion resistant container selected from a $ClO_2$ diffusion resistant polymer or glass, the molar ratio of chlorite ion to $ClO_2$ in said solutions ranging from about 20:1 to about 1:1, more preferably about 15:1 to about 1:1, most preferably about 10:1 to about 1:1. Preferred $ClO_2$ diffusion resistant polymers are selected from colorless polyethylene terephthalate (PETE) and fluorine-exposed polymers such as polyethylene. Preferred glass for use in the present invention includes both clear and pigmented or colored glass.

DETAILED DESCRIPTION OF THE INVENTION

The following terms are used throughout the present specification to describe the invention.

The term "$ClO_2$ diffusion resistant polymer or glass" is used throughout the specification to describe the materials from which containers which store $ClO_2$ solutions according to the present invention are made. Exemplary diffision resistant polymers for use in the present invention include, for example, polyethylene terephthalate (PETE) other than brown-tinted PETE and fluorine-treated polyethylene (high density or low density) or polypropylene. The glass or polymers, when fashioned into containers such as bottles etc., actually inhibit the diffusion of $ClO_2$ gas out of solution and into the atmosphere surrounding the container. Additional polymers which may be used in this aspect of the invention include any polymer which has been exposed to molecular fluorine in a fluorine treatment process, especially polyolefin polymers such as those derived from ethylene and propylene.. While not being limited by way of theory, it is believed that the fluorination treatment according to the present invention results in a polymer which has increased polarity, but which is denser in the sense of limiting free movement of $ClO_2$ through the polymeric structure. Thus, polymers which have a "tight" structure, are highly crosslinked and dense and are non-polar are ideal candidates for limiting the diffusion of $ClO_2$ out of an aqueous solution according to the present invention.

The term "impervious to the diffusional loss of $ClO_2$" or "essentially impervious to the diffusional loss of $ClO_2$" is used throughout the specification to describe the $ClO_2$ diffusion resistant polymer or glass containers which are used in the present invention which exhibit little, if any, loss of $ClO_2$ prior to unsealing the stored container (i.e., these containers storing $ClO_2$ solutions contain at least about 98% or more of the initial $ClO_2$ concentration after being stored for a period of three days and at least about 85% of the original $ClO_2$ in solution after a period of about 1 month). Further, these containers, in combination with $ClO_2$ formulations containing the approropriate chlorite/$ClO_2$ ratio as otherwise described herein, results in a storage stable formulation which contains at least about 75% of the initial concentration of $ClO_2$ in solution after significant periods of storage (i.e., about 6 weeks or more). One of ordinary skill can readily determine the type of container as well as the concentration of chlorite within the described ranges otherwise set forth herein to be added to the initial concentration of $ClO_2$ in order to provide stored/storage stable $ClO_2$ containing compositions according to the present invention.

Containers made of glass are also capable of preventing the release of $ClO_2$ in this aspect of the present invention. As used herein, the term glass is used as it is normally used by those of ordinary skill in the art. Glass is a hard, brittle substance, which, in this aspect of the present invention may be colorless or tinted, transparent or translucent, made by fusing silicates with soda or potash, lime and sometimes various metallic oxides. Many types of glass may be contemplated for use in the present invention, including crown glass, blown glass, tempered or toughened glass, etc. Preferred glass for use in the present invention includes, for example, any glass which is normally used to fashion glass bottles and glass containers, with tempered or toughened glass being preferred.

The term "$ClO_2$ solution" is used to describe an aqueous solution of $ClO_2$ which contains an amount of chlorite such that the molar ratio of chlorite to $ClO_2$ ranges from about 20:1 to about 1:1, more preferably about 15:1 to about 1:1 and most preferably about 10:1 to about 1:1. As used herein, a $ClO_2$ solution may contain numerous additional ingredients or components so long as those components do not substantially affect the storage stability of the $ClO_2$ solution in $ClO_2$ diffusion resistant containers which store the solutions. Additional ingredients which may be added to the present solutions include, for example, buffering agents, coloring agents, flavoring agents, surfactants, emulsifying agents, anti-caries agents and related components. One of ordinary skill will know to vary the amount and type of additives which may be included in formulations according to the present invention as a function of the end use for which a particular $ClO_2$ solution is to be used.

The term "salt of a chlorite" or "chlorite salt" is used throughout the specification to describe a salt of chlorite which is readily soluble in an aqueous system and which readily dissociates into a chlorite anion and counterion (generally, a metal cation). Two particularly preferred salts of chlorites for use in the present invention include sodium chlorite and potassium chlorite, although other chlorite salts may also be contemplated for use in the present invention. The term "chlorite" refers to $ClO_2^{13}$, which may be obtained from any chlorite salt source.

The term "acid" is used throughout the specification to describe protic acids, i.e., acids that release hydrogen ions in solution and combine with chlorite to produce chlorous acid, which disproportionates into $ClO_2$. Acids for use in the present invention include strong inorganic acids such as hydrochloric, sulfuric, sulfamic and nitric acid, preferably as dilute acid and organic acids such as acetic, citric, fumaric, glycolic, lactic, malic, mandelic, succinic, butyric and tartaric acid, among numerous others, as well as other acids such as sodium and potassium bisulfate ($NaHSO_4$ and $KHSO_4$) and phosphoric acid.

The term "storage stable" or "storage stability" is used throughout the present invention to describe $ClO_2$ solutions according to the present invention. Preferred $ClO_2$ solutions are storage stable, i.e., the solutions maintain a level (molar concentration) of $ClO_2$ in aqueous solution of at least about 98% for a period of at least about three days, at least about 85% for a period of at least about 1 month, about 75% of the original $ClO_2$ molar concentration for a period of at least about 6 weeks, more preferably at least about two months, even more preferably at least about 6 months and even more preferably at least a year or longer. In particularly preferred aspects of the present invention, the concentration of $ClO_2$ in storage stable solutions remains at a level of at least about 80% of the initial level, more preferably at least about 90% of the initial level, and even more preferably at least about 95% of the initial level. The term "initial level", "IL" or "initial concentration" is used to describe the concentration of $ClO_2$ in solution (generally, with reference to ppm) which is initially placed into or formed in a $ClO_2$ diffusion resistant container and then sealed. The term "measured level" or "ML" is used to describe the concentration of $ClO_2$ in solution after a particular measurement after the solution has been stored for a period of time, which is after the initial level is determined. Storage stability may be defined as ML/IL$\geq$0.98, 0.85 or 0.75, after a period of at least about three days, 1 month or six weeks, respectively. The term "sealed" is used to describe the storage containers containing compositions according to the present invention. By sealed, it is meant that the container is covered tightly (essentially air-tight) so that air, other gasses or solution cannot escape through the seal of the container.

The term "fluorine treated polymer" is used throughout the specification to describe a polymer, preferably a polyolefin such as (poly)ethylene or (poly)propylene which has been subjected to or treated with molecular fluorine ($F_2$) or a similar agent which fluorinates the polymer. The treatment is generally performed after the polymer is formed and molded into bottles or other containers. The fluorine treatment is believed to affect the polymer in a manner which creates increased polarity (due to the substitution of fluorine for hydrogen atoms within the polymer structure), but also the polymer is believed to be denser in the sense of limiting free movement of $ClO_2$ through the polymeric structure. Thus, polymers which have a "tight" structure, e.g., are highly crosslinked and dense and are non-polar (regardless of whether they are fluorinated or non-fluorinated) are ideal candidates for limiting the diffusion of $ClO_2$ out of an aqueous solution according to the present invention.

An exemplary fluorine treatment is available from Fluoro-Seal, Inc. of Houston, Tex. In this method, a polyolefin polymer such as (poly)ethylene or (poly)propylene which has been molded into an appropriate container is subjected to molecular fluorine for a time and at a concentration of fluorine gas which produces a fluorine seal in/on the treated polymer.

The present invention relates to storage stable $ClO_2$ solutions which are stored in $ClO_2$ diffusion resistant containers. The present invention is directed, therefore, to maintaining the initial concentration of $ClO_2$ in a solution in a continuous manner with minimal loss through degradation or through diffusion out of the walls of the containing vessel. A combination of a $ClO_2$ solution in a diffusion resistant container is another aspect of the present invention.

Several aspects of the present invention embrace the following concepts and/or results:

a)—That $ClO_2$ levels can be caused to remain stable in aqueous solution for prolonged periods, or even slowly increase, in the presence of defined chlorite ion-to-$ClO_2$ molar ratios, in the range of about 20:1 to about 1:1, more preferably about 15:1 to 1:1, even more preferably about 10:1 to about 1:1. Such stabilization is believed to be the result of the 1:1 complex of chlorite ion and $ClO_2$, identified as $Cl_2O_4$;

b)—That glass containers are particularly well suited to stably maintain aqueous $ClO_2$, solutions for prolonged periods;

c)—That certain plastic containers can similarly maintain $ClO_2$ solutons, with little or no diffusional losses, and that the same plastic container materials can be surprisingly induced to lose their ability to retain $ClO_2$ in solution by simple physical attachment of certain materials to their outer surfaces, without causing any structural change in the composition of the plastic itself;

d)—That a fluorine-gas treatment of certain plastic containers, which ordinarily allow diffusional losses of gaseous $ClO_2$ through their walls, will significantly reduce such diffusional losses, and surprisingly not have a similar retardant effect on gaseous oxygen.

In the present invention any manner of producing $ClO_2$ may be used, provided that the final solution contains chlorite anion in a molar ratio which is contemplated by the present invention to promote stability. While not being limited by way of theory, it is believed that the presence of chlorite in solution with $ClO_2$ within the prescribed molar ratios will produce a solution, which is storage stable for lengthy periods of time, ie. preferably for periods of at least about 6 weeks, more preferably at least about two months, even more preferably at least about 6 months and even more preferably at least a year or longer. Preferred methods for producing a $ClO_2$ solution include those which are described in U.S. Pat. No. 5,252,343 to Kross, et al. and U.S. Pat. No. 5,738,840 to Richter, both of which patents are incorporated by reference herein. One of ordinary skill will know to vary the method of obtaining $ClO_2$ solutions according to the end use.

The pH of the $ClO_2$ containing aqueous solutions of the present invention may vary over a range of about 4.0–4.5 to about 8.0, with a preferred range being about 5.0 to about 7.5, even more preferably about 5.5 to about 6.5.

Having generally described the invention, reference is now made to the following examples which are intended to illustrate preferred embodiments and comparisons but which are not to be construed as limiting to the scope of this invention as is more broadly set forth above and in the appended claims.

EXAMPLE 1

Stable $ClO_2$ in Aqueous Solution

The statement about $ClO_2$ by Wentworth, in U.S. Pat. No. 3,123,521, that it "decomposes rapidly, so that fresh solutions must be made up frequently" is characteristic of the current perception regarding the stability of aqueous $ClO_2$ solutions. This perception is affirmed by such experts in oxychlorine chemistry as Masschelein and Gordon, in the referenced publications on chlorine dioxide. It now appears, from my studies, that while that statement may be strictly true for pure $ClO_2$ solutions, the presence of a certain amount of chlorite ion ($ClO_2^-$) in the aqueous medium will help stabilize the presence of $ClO_2$ in that solution. This $ClO_2^-$ may be either a) added to the $ClO_2$ solution after it is formed; b) be residually present from incomplete oxidation of a $ClO_2^-$ solution to $ClO_2$; or c) result from the initial degradation of a pure $ClO_2$ solution, where some of the $ClO_2$ is reduced back to $ClO_2^-$.

The effect of the presence of $ClO_2^-$ in $ClO_2$ solutions is demonstrated in the following Table 1, where $ClO_2$ solutions were stored for prolonged periods in 16-oz glass bottles, at room temperature. One solution had virtually no excess $ClO_2^-$ initially present, another had $ClO_2^-$ initially present in an approximate molar ratio of 1:1 with respect to the $ClO_2$, and the other had an initial $ClO_2^-$ concentration corresponding to a molar ratio of ~14:1 with respect to the $ClO_2$.

TABLE 1

| $ClO_2$ Loss Through Glass (after # of days) ($ClO_2$ levels in ppm) | | | | | |
|---|---|---|---|---|---|
| High Chlorite[1] | | Low Chlorite[2] | | Minimum Chlorite[3] | |
| 1 hr | 43.9 | 2 hr | 32.6 | 2 hr | 25.2 |
| 2 | 44.2 | 1 | 32.2 | 1 | 24.4 |
| 5 | 44.4 | 4 | 31.6 | 3 | 23.6 |
| 9 | 46.0 | 6 | 31.2 | 9 | 22.7 |
| 13 | 46.8 | 11 | 30.4 | 14 | 21.8 |

TABLE 1-continued

| $ClO_2$ Loss Through Glass (after # of days) ($ClO_2$ levels in ppm) | | | | | |
|---|---|---|---|---|---|
| High Chlorite[1] | | Low Chlorite[2] | | Minimum Chlorite[3] | |
| 17 | 46.7 | 14 | 30.1 | 18 | 21.1 |
| 22 | 47.2 | 20 | 29.6 | 21 | 20.6 |
| 27 | 47.0 | 25 | 28.9 | 28 | 19.8 |
| 31 | 48.1 | 32 | 28.0 | 35 | 18.7 |
| 38 | 48.2 | 39 | 27.3 | 42 | 17.5 |
| 47 | 49.0 | 46 | 26.7 | | |
| 51 | 48.8 | 53 | 25.6 | | |
| 55 | 49.0 | | | | |
| 61 | 49.4 | | | | |
| 68 | 49.5 | | | | |
| 77 | 50.1 | | | | |
| 82 | 49.9 | | | | |

[1]Chlorite/$ClO_2$ ratio = ~14:1
[2]Chlorite/$ClO_2$ ratio = ~1:1
[3]Chlorite/$ClO_2$ ratio = ~0

The solutions were created by the addition of a known amount of sodium hypochlorite to a solution of sodium chlorite, of known concentration, with a pH initially adjusted to about 5.0–5.5 with citric acid. As noted in the third column, with minimum chlorite ion present initially (<~1 ppm), the $ClO_2$ loss is about 5% per week of its initial level, at a fairly constant rate over the 6 weeks of test. The low chlorite solution, with a higher chlorite level, only loses about 2.8% pre week of its initial content over the 7 ½ weeks of measurement. On the other hand, when a high level of $ClO_2^-$ is first present, the $ClO_2$ level, initially at ~40 ppm, actually rises at a decreasing rate for a finite period (~6 weeks), and then stabilizes thereafter for several months near 50 ppm. In this particular case, the increased $ClO_2$ is formed at the expense of some $ClO_2^-$ ion, where slow disproportionation of the chlorite that exists in small degree as the corresponding acid, chlorous acid (HClO), leads to increased levels of $ClO_2$. At that point, apparently, the $ClO_2^-$ : $ClO_2$ molar ratio is in the optimum range for maintaining a constant $ClO_2$ level thereafter. In this case the ratio is approximated as 12:1. Undoubtedly the range encompasses many higher and lower ratios, which also is a function of the initial pH of the system, where the acidity determines how much of the $ClO_2^-$ transforms to $ClO_2$. As acidity is consumed by chlorous acid degradation, the transformation diminishes, so the process is self-limiting.

The basis for the stability of the $ClO_2$ in the presence of $ClO_2$ ion appears to derive from the reported existence of a bimolecular charge-transfer complex involving one molecule each of $ClO_2$ and $ClO_2^-$, as follows:

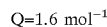

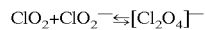

Thus, in solutions that contain both $ClO_2$ and $ClO_2^-$, it can be expected that a portion of the $ClO_2$ will be tied up in complex form, and not be available per se as free $ClO_2$. However it should be also noted that the oxidation potential of $[Cl_2O_4]^-$ is reportedly higher than that of $ClO_2$, so that $ClO_2$ solutions also containing $ClO_2^-$, and therefore the complex, ion would be expected to have a greater oxidation capacity than might be expected from simply that calculated from the level of $ClO_2$ present. This increased capacity would be expected to be associated with, for example, greater disinfection or a greater ability to destroy oral malodorants than a comparable $ClO_2$ solution with no additional chlorite present.

On the basis of the above data, and the theory underlying the need for a specific minimum amount of $ClO_2^-$ ion to be present with respect to $ClO_2$ in order for $ClO_2$ to achieve a certain level of stability in the aqueous solution, the molar ratio of $ClO2^-$: $ClO_2$ preferably should be at least 1:1, but not more than about 20:1. Above that relative amount of chlorite ion with respect to chlorine dioxide, a significant generation of $ClO_2$ from the $ClO_2^-$ will tend to create an undesired increase of $ClO_2$ in the aqueous solution over a period of time, rather than maintaining a fairly constant level.

EXAMPLE 2

Suitability of Glass Containers

The ability of $ClO_2$ to remain in a stable state in glass containers was found to be different when similar solutions were stored in several other plastic containers. Specifically 16 oz bottles of two other plastic materials, polyvinyl chloride (PVC) and high density polyethylene, were filled with a chlorite solution, acidified with citric acid and reacted with equal amounts of sodium hypochlorite. The final pH's of all these solutions were ~5.7, and had $ClO_2^-$: $ClO_2$ ratios of ~14:1. The containers were then stored at ambient conditions for about a month, and periodic readings taken of their $ClO_2$ levels, using a spectrometer at 360 nM; an extinction coefficient of $e=1242$ liter mol$^{-1}$ cm$^{-1}$, was used to calculated concentrations from absorbance readings. The readings were compared with the first month's data shown for the solution in the glass container provided earlier, which had a similar molar ratio and pH. They were as follows:

$ClO_2$ LEVELS IN SOLUTIONS STORED IN VARIOUS 16 oz BOTTLES

| TIME (days) | GLASS | POLYVINYL CHLORIDE ppm | HIGH DENSITY POLYETHYLENE |
|---|---|---|---|
| 1 hr. | 43.9 | 35.0 | 34.8 |
| 2 | 44.2 | 32.6 | — |
| 3 | — | — | 29.0 |
| 4 | — | 30.4 | — |
| 5 | 44.4 | — | 27.3 |
| 7 | — | — | 25.4 |
| 8 | — | 25.7 | — |
| 9 | 46.0 | — | — |
| 10 | — | — | 22.9 |
| 11 | — | 22.6 | — |
| 13 | 46.8 | — | — |
| 14 | — | 20.2 | 20.0 |
| 17 | 46.7 | — | — |
| 18 | — | — | 17.4 |
| 21 | — | 15.9 | — |
| 22 | 47.2 | — | — |
| 24 | — | 14.3 | 14.1 |
| 27 | 47.0 | — | — |
| 28 | — | — | 12.2 |
| 30 | — | 12.3 | — |
| 31 | 48.1 | — | — |
| 32 | — | — | 9.9 |
| % loss at end | (+)9.6% | 64.9% | 71.6% |

The data show that, unlike the glass container, the two common plastic containers lose significant quantities of $ClO_2$ over approximately 1 month's time, where the PVC container contains 64.9% less $ClO_2$ than originally present, and the polyethylene container 71.6% of the original level. The losses are actually greater, however, corresponding to about 68% and 74% respectively, when taking into account the $ClO_2$ levels that would be present after the one month's $ClO_2$ buildup. It is of particular interest to note that the high density polyethylene container is the one that is currently being used by the company marketing an oral rinse malodorant solution containing free molecular $ClO_2$, in contradistinction to those selling chlorite solution termed "stabilized chlorine dioxide." The container is provided with a chlorite solution, to which an acid and a hypochlorite concentrate are added by the consumer, immediately prior to use to generate a 14-day supply of $ClO_2$ solution. At the end of that period, the final solution will contain less than 60% of the initial $ClO_2$, which lowers the efficiency of the oral malodorant to correct the user's bad breath. A glass container is often too costly and fragile, for both shipping and normal bathroom storage, and common plastic containers such as PVC and polyethylene limit the shelf-life and volume of $ClO_2$ solution that can be prepared at any one time. However under certain usage conditions, glass has hereby been shown to be suitable for the storage of $ClO_2$ solutions, provided that the $ClO_2^-/ClO_2$ ratio lies between about 1:1 and about 20:1.

EXAMPLE 3

Suitability of a Specific Plastic Container for Retaining $ClO_2$, in Solution During the evaluation of plastic containers for such storage, tests were conducted on 16 oz bottles of high density polyethylene terephthalate (PETE). The bottles received for such study were colorless and transparent. Since $ClO_2$ and $ClO_2^-$ solutions are reportedly sensitive to the presence of light, which hastens their degradation, the outer surfaces of the clear bottles were covered with a translucent plastic tape. When a $ClO_2$ solution containing $ClO_2^-/ClO_2$ at a 14:1 molar ratio was stored in that container, the solution lost $ClO_2$ in a manner already seen for the other plastic containers. Similar losses were shown for a brown-tinted 16-oz PETE container. As a negative control, a similar solution was evaluated in the clear PETE container, and surprisingly the loss of $ClO_2$ was minimal, over a protracted period of time. The data were as follows:

$ClO_2$, Levels in Different Polyethylene Terephthalate 16 oz Containers

| STORAGE TIME (Days) | Translucent Surface | Brown Tinted ppm | Clear, Colorless in the light | in the dark |
|---|---|---|---|---|
| 0 | 35.2 | 25.5 | 34.5 | 33.2 |
| 2 | — | 24.4 | — | 32.9 |
| 3 | 25.0 | — | 35.0 | — |
| 4 | — | — | — | 33.0 |
| 5 | 23.9 | — | 35.1 | — |
| 7 | 23.0 | — | 35.0 | — |
| 8 | — | 22.4 | — | 33.0 |
| 10 | 21.7 | — | 35.1 | — |
| 11 | — | — | — | 33.0 |
| 14 | 20.5 | 21.7 | 35.0 | 32.8 |
| 17 | — | 21.3 | — | — |
| 18 | 19.3 | — | 35.0 | — |
| 21 | — | — | — | 32.7 |
| 24 | 17.9 | — | 34.9 | 32.8 |
| 28 | 17.1 | — | 34.8 | — |
| 30 | — | — | — | 32.7 |
| 32 | 16.1 | — | 34.4 | — |
| 35 | — | — | — | 32.8 |
| 38 | 15.2 | — | 34.1 | — |
| 45 | 14.2 | — | 33.8 | — |

-continued $ClO_2$, Levels in Different Polyethylene Terephthalate 16 oz Containers

| STORAGE TIME (Days) | Translucent Surface | Brown Tinted | Clear, Colorless in the light | Clear, Colorless in the dark |
|---|---|---|---|---|
| | | ppm | | |
| 48 | — | — | 33.8 | — |
| 54 | — | — | 33.6 | — |
| 59 | — | — | 33.3 | — |
| ppm loss/week* | 3.3 | 12 | 0.14 | 0.08 |

*dividing total loss of $ClO_2$ by fractional weeks of study.

It was determined that the clear PETE bottle, with a taped outer surface, lost about 42% of the $ClO_2$ in a two week period, while solutions with the same $ClO_2$ levels, in identical bottles, under both light and dark storage conditions, sustained little perceptible losses. On average over the length of the three studies, the $ClO_2$ loss from the two clear, uncovered bottles averaged about 0.1 ppm per week, while the loss from the identical bottle with the surface covered averaged about 3.3 ppm. The 0.1 ppm loss could well have arisen from slight headspace losses of $ClO_2$, associated with the intermittent spectrophotometric readings. It is concluded that the clear PETE container represents a practical means to store $ClO_2$ in aqueous solution, providing that its outer surface is not covered, at least with an adhesive material. The losses observed with the brown tinted container, without outer covering, strongly suggests that $ClO_2$, containment and losses through wall permeation is not related to light effects, since no losses occurred from a soultion stored in the dark in a clear PETE bottle. Rather it appears to be intimately associated with static charge, or related electric effects of the plastic container. This conclusion is consistent with observations from the next example of this invention description.

EXAMPLE 4

Fluorine Gas Treatment Effects

The relative low cost of high density polyethylene and polypropylene containers, in addition to their good mechanical and thermal properties, led to investigations to determine whether some treatment of these containers might minimize diffusional losses of $ClO_2$. One treatment considered was the use of fluorine, which has shown some value in transforming the surfaces of these containers so as to reduce the absorption on non-polar hydrocarbons, such as flavors and fragrances, from container contents. When this absorption occurs it reduces the concentration of these materials in the contents. The treatment, however, is not reported to minimize gaseous diffuision through the treated walls, such as by oxygen, so that little positive effects were anticipated.

HDPE 16-oz bottles, of the type used for a $ClO_2$-containing oral malodorant, were exposed to a Stage 1 fluorine treatment by Fluoro-Seal, Inc. of Houston, Tex. Thereafter, duplicate sets of $ClO_2$ solutions were activated in these containers, using the acid/hypochlorite system described above. The $ClO_2$ levels of the two solutions were then measured over a 45 day period. The resulting data are shown in the following Table, where it can be seen that the $ClO_2$ loss from the fluorine-treated container averages less than 50% of that from the untreated container over that time. This is a surprising difference, when considering the reported inability of oxygen ($O_2$), a smaller molecule than $ClO_2$, to be retarded in trans- wall permeation by a fluorinated surface. The difference in diffusion rates is attributed to $ClO_2$'s polarity; the molecule being paramagnetic with a single unpaired electron, i.e. it is a stable free radical. $O_2$ is electrically symmetrical and non-polar. This difference may shed some light on the non-diffusion of $ClO_2$ through a clear PETE container, but not through one where its electrical or its static-charge characteristics may be modified by either an adhesive surface or a tinting agent incorporated into the polymer itself. The taped surface may allow for a neutralization of any static charge on the surface of the PETE container, which would otherwise suppress $ClO_2$ loss through the walls.

It is anticipated that different degrees of fluorination of HDPE, or polypropylene, or of other plastic materials such as tinted PETE, will show even greater suppressive action with respect to the diffsuional losses sustained by $ClO_2$.

$ClO_2$ Loss through Fluorine-Treated HDPE, vs. Control (ppm)

| TIME (days) | Fluorinated | Control |
|---|---|---|
| 0 | 33.5 | 34.8 |
| 3 | 32.9 | 29.0 |
| 5 | 32.2 | 27.3 |
| 7 | 31.5 | 25.4 |
| 10 | 30.5 | 22.9 |
| 14 | 29.1 | 20.0 |
| 18 | 27.4 | 17.4 |
| 24 | 24.8 | 14.1 |
| 28 | 23.0 | 12.2 |
| 32 | 21.0 | 9.9 |
| 38 | 18.4 | 7.3 |
| 45 | 15.4 | 4.9 |
| $ClO_2$ loss/week | 2.8 | 4.7 |

EXAMPLE 5

$ClO_2$-containing Oral Malodorant Solution

This example demonstrates the preparation of a $ClO_2$-containing oral malodorant solution and the composition of a plastic container for the home preparation and twice-daily use of this oral malodorant which, once activated, is appropriately stable for a two-week period. A 16-oz bottle of high density polyethylene is first subjected to a fluorine gas treatment, characterized as a "Stage 1 Fluorination." by Fluoro-Seal, Inc. Of Houston, Tex. To that bottle is added 463 ml of a sodium chlorite solution at a concentration of 0.090%. The sodium chlorite is partially oxidized by the user by adding 5 ml of a citric acid concentrate to reduce the pH to about 5.5, followed by addition of 5 ml of a solution containing 17.9 mg of sodium hypochlorite. This forms a $ClO_2$ solution with a concentration of about 35 ppm, and a residual chlorite ion level of about 622 ppm, with a $ClO_2^-$/$ClO_2$ molar ratio is about 18:1.

EXAMPLE 6

The $ClO_2$ oral-malodorant solution described in Example 5 is prepared, in bulk, and 473 ml (16 fl oz) of the solution are added to clear, high density polyethylene bottles. These solutions are placed in mailing containers, with 6 month shelf-life labels, and shipped to consumers worldwide.

EXAMPLE 7

This example demonstrates the preparation of a stable $ClO_2$-containing aqueous solution for multiple uses, such as a surface disinfectant, a toilet-bowl stain-remover and disinfectant, a disinfectant for fruits, vegetables and meats, and as an oral malodorant rinse. The solution is prepared in bulk by acidifying a 200 ppm sodium chlorite solution to pH 5.8 with citric acid, then adding 27.6 mg of sodium hypochlorite per liter of adjusted solution, stirring and storing the solution for about one hour prior to bottling it into suitably sized glass containers. The solution contains about 25 ppm of $ClO_2$, and a residual chlorite ion level such that the initial $ClO_2^-/ClO_2$ ratio is about 5:1. It has a shelf-life in excess of 1 year.

While the invention has been described in reference to the specific embodiments, it should be understood by those skilled in the art that various changes can be made and equivalents can be substituted without departing from the true spirit and scope of the invention. All such modifications are intended to be within the scope of the claims appended hereto.

What is claimed is:

1. A method of storing an aqueous $ClO_2$ composition consisting essentially of an aqueous solution of $ClO_2$ comprising a concentration of $ClO_2$ ranging from about 1 ppm to about 500 ppm in combination with chlorite, wherein the molar ratio of chlorite to $ClO_2$ ranges from about 1:1 to about 20:1, said method comprising storing said aqueous solution in a sealed container impervious to the diffusional loss of $ClO_2$ said container consisting essentially of a diffusion resistant polymer selected from the group consisting of polyethylene terephthalate other than brown-pigmented polyethylene terephthalate, and a fluorine-treated polymer.

2. The method according to claim 1 wherein said composition is stored for a period of at least about six weeks prior to unsealing and maintains a concentration of $ClO_2$ of at least about 75% of its initial concentration after said period.

3. The method according to claim 1 wherein said ratio of chlorite to $ClO_2$ ranges from about 1:1 to about 10:1.

4. The method according to claim 1 wherein said $ClO_2$ comprises at least about 5 ppm.

5. The method according to claim 1 wherein said chlorite is obtained from sodium chlorite or potassium chlorite.

6. The method according to claim 1 wherein said polyethylene terephthalate polymer is colorless, blue or opaque polyethylene terephthalate.

7. The method according to claim 1 wherein said fluorine-treated polymer is a fluorine-treated (poly)olefin polymer.

8. The method according to claim 1 wherein said composition maintains a concentration of $ClO_2$ of at least about 75% of its initial concentration for a period of at least about 6 months.

9. The method according to claim 1 wherein said composition maintains a concentration of $ClO_2$ of at least about 75% of its initial concentration for a period of at least about 1 year.

10. The method according to claim 7 wherein said fluorine-treated polymer is selected from the group consisting of fluorine-treated (poly)ethylene and fluorine-treated (poly)propylene.

* * * * *